United States Patent [19]
Provost et al.

[11] Patent Number: 5,953,797
[45] Date of Patent: *Sep. 21, 1999

[54] HOOK FASTENERS AND METHODS OF MANUFACTURE

[75] Inventors: George A. Provost, Litchfield, N.H.; Mark J. Condon, Melrose, Mass.; A. Todd Leak, Neenah, Wis.; Apiromraj S. Roslansky, Little Chute, Wis.; Paul J. Serbiak, Appletone, Wis.

[73] Assignee: Velcro Industries B.V., Curacao, Netherlands

[*] Notice: This patent issued on a continued prosecution application filed under 37 CFR 1.53(d), and is subject to the twenty year patent term provisions of 35 U.S.C. 154(a)(2).

[21] Appl. No.: 08/731,061

[22] Filed: Oct. 9, 1996

[51] Int. Cl.⁶ ................................. A44B 18/00
[52] U.S. Cl. ........................ 24/452; 24/304; 24/442; 24/446
[58] Field of Search ................. 24/452, 442, 445, 24/446, 448, 304

[56] References Cited

U.S. PATENT DOCUMENTS

| | | | |
|---|---|---|---|
| 3,031,730 | 5/1962 | Morin | 24/452 |
| 3,138,841 | 6/1964 | Naimer | 24/204 |
| 3,147,528 | 9/1964 | Erb | 24/204 |
| 3,192,589 | 7/1965 | Pearson | 24/204 |
| 3,261,069 | 7/1966 | Mathison | 24/204 |
| 3,607,995 | 9/1971 | Chiba | 264/15 |
| 3,718,725 | 2/1973 | Hamano | 264/163 |
| 3,770,359 | 11/1973 | Hamano | 425/305 |
| 3,785,012 | 1/1974 | Billarant | 24/204 |
| 3,808,301 | 4/1974 | Pruden | 24/80 |
| 3,808,648 | 5/1974 | Billarant et al. . | |
| 3,900,652 | 8/1975 | Uraya et al. | 428/92 |
| 4,169,303 | 10/1979 | Lemelson | 24/452 |
| 4,290,174 | 9/1981 | Kalleberg | 24/204 |
| 4,454,183 | 6/1984 | Wollman | 428/92 |
| 4,628,709 | 12/1986 | Aeschbach et al. . | |
| 4,770,917 | 9/1988 | Tochacek et al. | 428/95 |
| 4,794,028 | 12/1988 | Fischer . | |
| 4,846,815 | 7/1989 | Scripps | 604/391 |
| 4,984,339 | 1/1991 | Provost et al. | 24/452 |
| 5,077,870 | 1/1992 | Melbye et al. . | |
| 5,131,119 | 7/1992 | Murasaki et al. | 24/452 |
| 5,230,851 | 7/1993 | Thomas | 264/145 |
| 5,315,740 | 5/1994 | Provost . | |
| 5,326,612 | 7/1994 | Goulait | 428/100 |
| 5,339,499 | 8/1994 | Kennedy et al. . | |
| 5,393,475 | 2/1995 | Murasaki et al. . | |
| 5,625,930 | 5/1997 | Takizawa et al. | 24/452 |
| 5,679,302 | 10/1997 | Miller et al. . | |
| 5,685,050 | 11/1997 | Murasaki | 24/452 |
| 5,692,271 | 12/1997 | Provost et al. | 24/452 |
| 5,749,129 | 5/1998 | Murasaki et al. . | |
| 5,755,015 | 5/1998 | Akeno et al. . | |
| 5,781,969 | 7/1998 | Akeno et al. . | |
| 5,792,408 | 8/1998 | Akeno et al. . | |

FOREIGN PATENT DOCUMENTS

| | | |
|---|---|---|
| B-70529/96 | 3/1997 | Australia . |
| 0 811 331 A2 | 12/1997 | European Pat. Off. . |
| 6-133808 | 5/1994 | Japan . |
| 294586 | 1/1997 | Taiwan . |
| 2 279 106 | 12/1994 | United Kingdom . |
| WO 94/23610 | 10/1994 | WIPO . |
| WO 94/29070 | 12/1994 | WIPO . |
| WO 95/05140 | 2/1995 | WIPO . |

*Primary Examiner*—Victor N. Sakran
*Attorney, Agent, or Firm*—Fish & Richardson P.C.

[57] ABSTRACT

A hook fastener member having rows of molded hook-shaped fastener elements that lie in planes aligned with the rows, with generally planar plate portions at the outermost ends of at least some of the fastener elements, the plate portions lying generally parallel to the base of the fastener member. The plate portions can enhance engagement of the hook fastener members with mating loop fastener members, particularly with low loft non-woven loop fastener members. A method of making fastener members is provided. Molten resin is extruded and applied to a molding roller, creating preforms. The outermost portions of at least some of the preforms are flattened, thereby forming generally plate shaped portions. Disposable absorbent garments advantageously incorporate the hook fastener members.

19 Claims, 10 Drawing Sheets

HOOK FASTENERS AND METHODS OF MANUFACTURE

BACKGROUND OF THE INVENTION

The invention relates to improved hook members for hook-and-loop fastening and methods of manufacturing hook members.

In general, hook-and-loop fasteners comprise two mating components: a hook member that has upstanding, hook-type fastener elements, and a loop member that has a surface that provides fibers or fiber loops with which the hook elements become engaged.

As used here, a "hook member" means a member having fastener elements whose hooks extend substantially in a given plane. When of molded form, the stems of these elements are significantly broader in the direction of their plane of extent than in the thickness direction at a right angle thereto.

Hook fasteners are often preferred over other types of fasteners, for instance, those having mushroom-like form, because hook fasteners can provide more secure engagement with the loops, offer advantages in manufacturing, etc.

Loop members for hook-and-loop fastening have been comprised of knitted, woven, and non-woven textiles. A common example of a non-woven textile is known by the term "spun bonded." It is made by spinning fine filaments of plastic resin, e.g., polypropylene, and distributing them in superposed layers. The fibers are bonded to each other in random orientations, with a fine, low-lying, nappy layer of looped and arched fibers exposed at the surface of the fabric.

Because non-woven fabrics are inexpensive, they are desired for use as the loop part of fasteners for low cost items, particularly disposable products such as diapers, surgical gowns, and sanitary napkins. It is desirable to provide fastener members useful with very low cost, low loft non-wovens and other low loft fabrics.

SUMMARY OF THE INVENTION

One aspect of the invention relates to a fastener member useful for separable engagement with surface fibers of a low-loft, non-woven fabric or the like. The fastener includes a base and multiple rows of molded hook-form fastener elements extending from the base and exposed for engagement with the fabric. Each of the hook form fastener elements comprises a stem portion joined at one end to the base and at least one fiber-engaging hook-form portion joined at the opposite end of the stem portion and having a free end. The hook-form fastener elements lying substantially only in planes aligned with respective rows. At least some of the fastener elements include a fiber-engaging plate portion at the outermost portion of the hook-form portion, which plate portion lies generally parallel to the base. The plate portion provides an overhanging portion in the direction perpendicular to its row that can engage the surface fibers of the fabric.

Certain implementations of this aspect of the invention include one or more of the following features. The fastener member, in certain implementations, provides: a plate portion which has a thickness, in the direction normal to the base, that is less than the height, in the direction normal to the base, of the free end of the hook portion; fastener elements formed of thermoplastic resin, the stem portions of the elements being molded integrally with the base, and the plate portion comprising a post-formed structure formed from the resin of the uppermost portion of the molded fastener element; that substantially all the hook-form portions of the fastener elements in a first row extend in one direction along the row and substantially all the hook-form portions of the fastener elements in a neighboring second row extend in the opposite direction; that substantially all of the fastener elements include plate portions; that substantially all of the fastener elements in the first row contain a plate portion while substantially all of the elements in the neighboring second row do not; a stem portion which has substantially flat relatively broad sides, a cross-section of each stem portion, taken parallel to the base at the mid-height region of the stem, having a width in the direction of the row and a thickness in the direction perpendicular to the row, the width being about twice the thickness or more; a stem in which the width of the stem tapers from the base to the hook-form portion; a central axis of the stem is inclined, in the direction of the respective row, at a substantially acute angle relative to the base.

Another aspect of the invention relates to a fastener member useful for separable engagement with surface fibers of a low-loft, non-woven fabric or the like. The fastener comprises a base and multiple rows of molded fastener elements extending from the base. Each fastener element comprises a stem portion joined at one end to the base, the stem being inclined, at a substantially acute angle relative to the base in the direction of the respective row of the element, and lying substantially only in planes aligned with its respective row relative to the base, and a fiber-engaging plate portion disposed at the opposite, outermost end of the stem portion, the plate portion extending transversely to the direction of the respective row to form an overhang portion that can engage the surface fibers of the fabric.

Certain implementations of this aspect of the invention include one or more of the following features. The fastener member, in certain implementations, provides a cross-section of each stem portion, taken parallel to the base, has a width in the direction of the row and a thickness in the direction perpendicular to the row, the width being substantially greater than the thickness; that substantially all of the fastener elements include plate portions.

In accord with another implementation of the invention, a closure is provided comprising a fastener member as described above and a non-woven fabric engaged therewith, the base of the fastener and the non-woven fabric being under tension in opposite directions such that the fastener elements are subjected to and resist shear forces caused by the tension loading, the tension acting in the direction of the thickness of the stem portion.

Another aspect of the invention relates to a method for making fastener members comprising extruding molten resin and applying the resin to a molding roller having forming cavities around its perimeter. Pressure is applied to the resin to cause the resin to fill the cavities, thereby forming a fastener member preform, the fastener member preform comprising a base and a multiplicity of discrete fastener element preforms integrally molded with and extending from the base at a substantially acute angle, the fastener element preforms aligned in at least one row comprising stem portions with outermost ends lying over the base substantially only in planes aligned with its row. Fastener member preforms are stripped from the molding roller. The outermost portions of at least some of the fastener element preforms are flattened, thereby forming generally plate-shaped portions disposed at the outermost ends and generally parallel to the base and perpendicular to the row.

Certain implementations of this aspect of the invention include one or more of the following features. The method, in certain implementations, provides: the flattening comprises heating the outermost ends of at least some of the fastener element preforms to a temperature that is near the melt temperature of the resin and applying pressure to the outermost ends; the heating and the applying pressure are performed in a single step; the single step comprises passing the fastener member preforms by a heated roller and pressing at least some of the fastener element preforms against the heated roller; the fastener member preforms are formed and the outermost ends of at least some of the preforms are flattened as part of a single, continuous process; the outermost ends of at least some of the fastener element preforms are flattened in a post-processing operation; prior to the flattening, differences in the heights of the fastener element preforms are corrected to ensure generally uniform height; the correcting comprises pressing a knock-down roller against the outermost ends of the fastener element preforms; that substantially all of the fastener elements are flattened; that a product is formed by the method.

In another aspect of the invention, the outermost portions of some fastener elements are farther away from the base, as formed, than the outermost portion of at least some other fastener elements. At least some of the outermost portions farthest away from the base are then flattened, forming generally plate-shaped portions disposed at said outermost ends and generally parallel to the base and perpendicular to the row.

In a preferred embodiment, stripping the preforms from the molding roller causes the fastener members extending in one direction to be deformed to be of greater height than fastener members in another direction.

Another aspect of the invention relates to a method for improving the engageability of a hook-type fastener member with a non-woven loop-type fastener member. The hook-type fastening member comprising a base and a multiplicity of generally hook-shaped fastener elements integrally molded with and extending from the base in a given direction or in that direction and the opposite direction and lying only in planes parallel with the given direction and perpendicular to the base. The method comprises flattening outermost ends of at least some of the fastener elements to form generally plate-form portions disposed at the distal ends and generally parallel to the base and perpendicular to the planes.

The new hook fastener members are well suited for engagement with low loft non-woven loop members since the outer plate portions of the fastener elements that overhang the sides of the elements are able to slide under and initially engage the surface fibers of the loop member. This feature can improve the level of engagement of the fastener, especially when the fastener elements are subjected to shear forces acting sideways relative to the direction of the plane of the hook elements. The flat-top hook fastener elements, while providing the secure engagement by the hooks, also can avoid skin irritation since the area of contact between the skin and the fastener elements is relatively large. This is of particular value when a hook fastener comes in contact with the skin of babies. Finally, these hook fasteners can be manufactured using conventional hook-member tooling with simple additional post-molding steps.

Other aspects of the invention concern a disposable absorbent garment having first and second opposed longitudinal end portions, and comprises an outer cover; a body-side liner; an absorbent core located between the outer cover and the body-side liner; a loop member operably associated with the garment; and a fastener member operably associated with the garment for separable engagement with the loop member, the fastener member comprising: a base; and multiple rows of molded hook-form fastener elements extending from the base.

According to one aspect of the invention, the fastener elements are exposed for engagement with the loop member, each of the hook-form fastener elements comprising a stem portion joined at one end to the base and at least one fiber-engaging hook-form portion joined at the opposite end of the stem portion and having a free end, the hook-form fastener elements lying substantially only in planes aligned with respective rows. At least some of the fastener elements include a fiber-engaging plate portion at the outer most portion of the hook-form portion, the plate portion lying generally parallel to the base, the plate portion providing an overhang portion in the direction perpendicular to its row.

Certain implementations of this aspect of the invention have one or more of the following features.

The plate portion has a thickness, in the direction normal to the base, that is less than the height, in the direction normal to the base, of the free end of the hook portion. The stem portion has substantially flat relatively broad sides, a cross-section of each stem portion, taken parallel to the base at the mid-height region of the stem, having a width in the direction of the row, and a thickness in the direction perpendicular to the row, the width being about twice the thickness or more.

Certain advantageous implementations of this aspect of the invention have one or more of the following features. The loop member comprises a nonwoven material. The loop member is joined to the outer cover in the first opposed longitudinal end section and the fastener member is operably associated with the second opposed longitudinal end section, preferably the garment 25 having a longitudinal axis and wherein the fastener elements are oriented parallel to the longitudinal axis of the garment.

According to another aspect of the invention concerning the disposable absorbent garment, each of the fastener elements comprise a stem portion joined at one end to the base, the stem being inclined at a substantially acute angle relative to the base, in the direction of the respective row of the fastener element and lying substantially only in planes aligned with its respective row. At least some of the elements also comprise a fiber-engaging plate portion disposed at the opposite, outermost end of the stem portion, the plate portion extending transversely to the direction of the respective row to form an overhang portion.

In preferred embodiments of the aspect of the invention, a cross-section of each stem portion, taken parallel to the base, has a width in the direction of the row and a thickness in the direction perpendicular to the row, the width being substantially greater than the thickness.

Certain advantageous implementation of both of these aspects of the invention include that substantially all of the fastener elements include plate portions.

BRIEF DESCRIPTION OF THE DRAWINGS

FIG. 5 is a schematic "peer-through window" view illustrating the engagement of a hook fastener element with a non-woven loop member while

EMBODIMENTS

A preferred embodiment 110 of a hook fastener member, particularly useful on disposable diapers, is shown in FIGS. 1, 1a, 1b, 1c, and 2. The hook fastener member consists of a base sheet 112 and multiple parallel rows of integrally molded hook-form fastener elements 114 extending from the base sheet. Although only three rows are shown in several of the figures, it is to be understood that the fastener member may comprise several rows.

Figure 1:
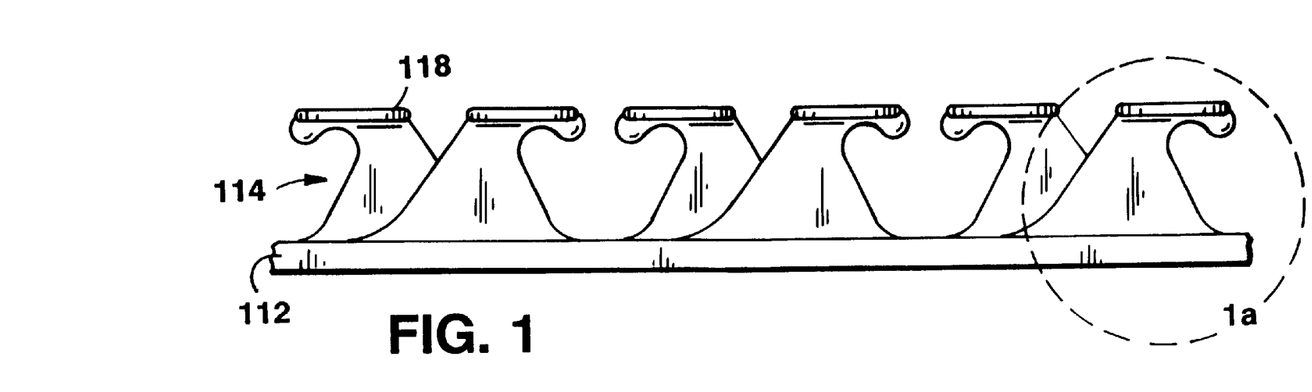
FIGS. 1 and 2 are side elevational and plan views, respectively, showing one embodiment of a hook fastener member.
Figure 1A:
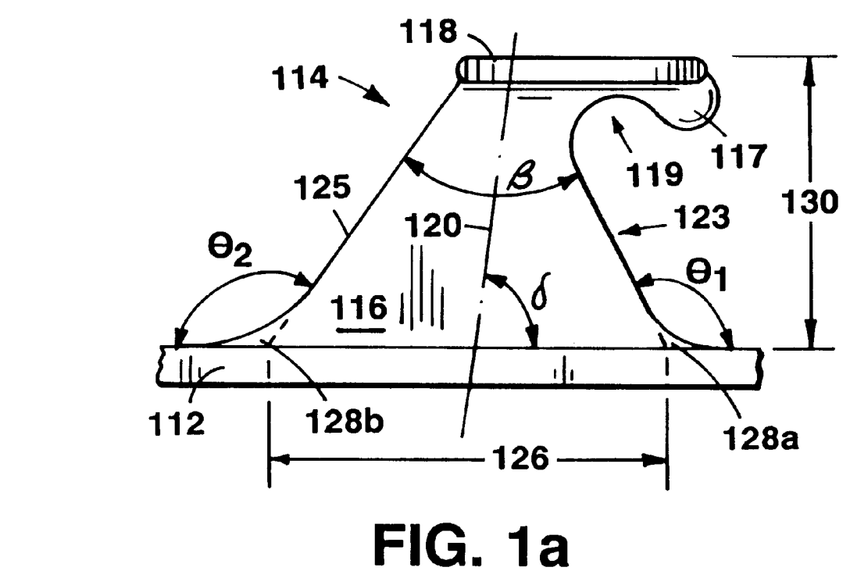
FIGS. 1a, 1b, and 1c are detailed side elevational, end, and plan views, respectively, showing a single fastener element of the fastener member in FIG. 1.
Figure 1B:
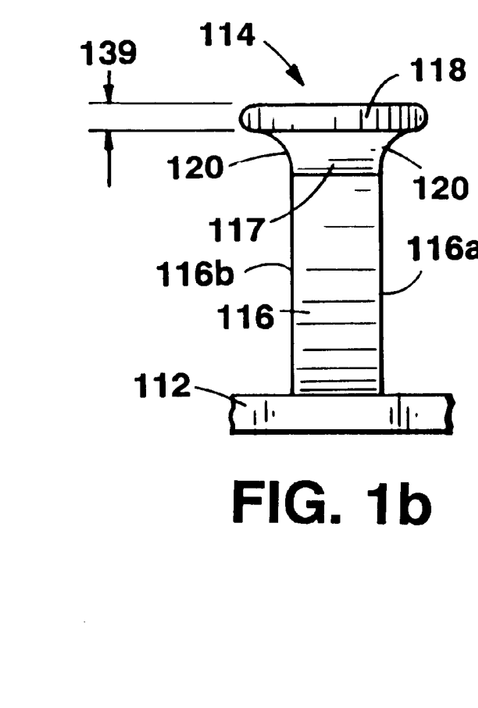
Figure 1C:
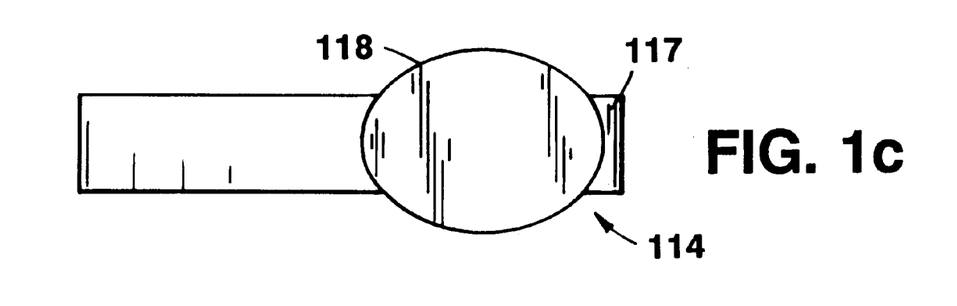

As shown in greater detail in FIGS. 1a–1c, each fastener element of FIG. 1 has a stem portion 116 of uniform thickness that has flat vertical sides 116a, 116b that extend normal to the plane of the base sheet 112. Joined to the upper end of the stem is a re-entrant, hook-form portion 117 that engages loops or fibers. At the top of the fastener is joined a thin, generally disk-shaped outer plate portion 118 oriented substantially parallel to the base sheet.

The re-entrant hook-form portion curves over and down toward the base sheet from the upper end of the stem portion 116 to define a fiber-retaining recess 119 on the underside of the hook-form portion.

Figure 2:
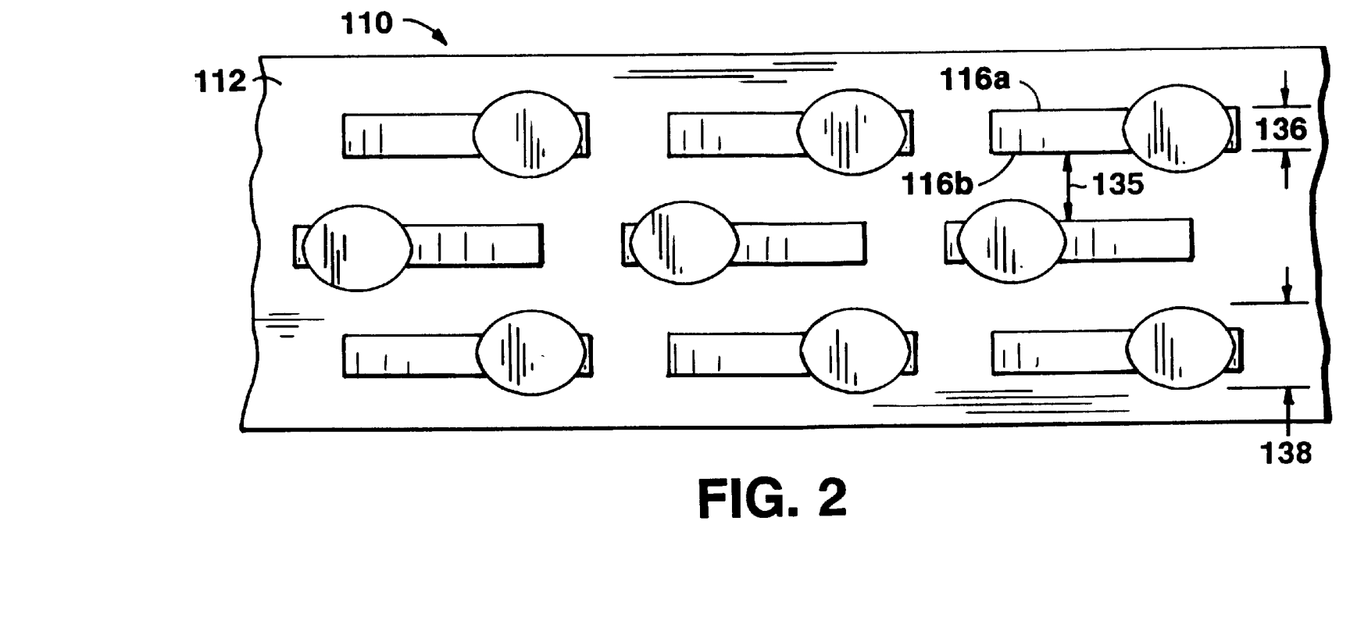

The stem portion in side elevation, as seen in FIG. 1a, tapers outwardly from a wide base to a relatively narrow outer portion in the region of the recess 119. The fastener elements are generally aligned in multiple rows parallel with the flat sides of the individual elements, and the outer plate portion of each fastener element has portions that extend transversely, to overhang the sides 116a, 116b of the fastener element (FIGS. 1b, 1c, 2).

In this preferred embodiment, the edge surfaces 123, 125 of the stem portion form angles $\theta_1$ and $\theta_2$ relative to the base sheet, respectively, that are substantially greater than ninety degrees. Preferably, $\theta_1$ and $\theta_2$ are between about 30 and 160 degrees. More preferably, they are each about 115 degrees and 125 degrees, respectively. Forming the stem portion such that the edges are straight or slant inward allows the preform to be removed more easily from the molding roller 50 because the hook-form portion 117 can pass more easily through the portion of the molding roller in which the stem portion was formed.

For use in an important application for the new fastener, in conjunction with non-woven loop members, the fastener elements are generally quite small. Hence, height 130 of the fastener element 114 is preferably between about 0.005 inch and about 0.030 inch, with about 0.0150 inch being most preferred. Furthermore, the base width 126—i.e., the width of the stem portion, taken parallel to the base sheet 112 at the level where the stem portion joins the base sheet, disregarding the fillets 128a and 128b—is preferably between about 0.010 inch and about 0.025 inch, with about 0.0170 inch being most preferred.

Furthermore, the fastener elements are provided in relatively high density, for example, from about 500 to about 4,000, alternatively from about 1,000 to 2,500, alternatively from about 1,500 to about 2,000 fastener elements per square inch. For example, as shown in FIG. 2, the elements preferably are spaced apart laterally a distance 135 of about 0.008 inch, and the stem portions 116 preferably have a thickness 136 of about 0.006 lineal inch. This yields a widthwise density of approximately 71 fastener elements per inch. In the lengthwise direction, there are preferably about 24 fastener elements per lineal inch. Hence, there are preferably on the order of 1700 fastener elements per square inch in this preferred embodiment.

A distinctive feature of the hook-form fastener element 114 is the presence of the plate portion 118. This feature contributes to making the hook fastener embodiment 110 particularly useful for engaging the loops of non-woven fabrics in general and, in particular, the low-loft non-woven fibers desired to be used on disposable diapers.

Figures 3, 3A:
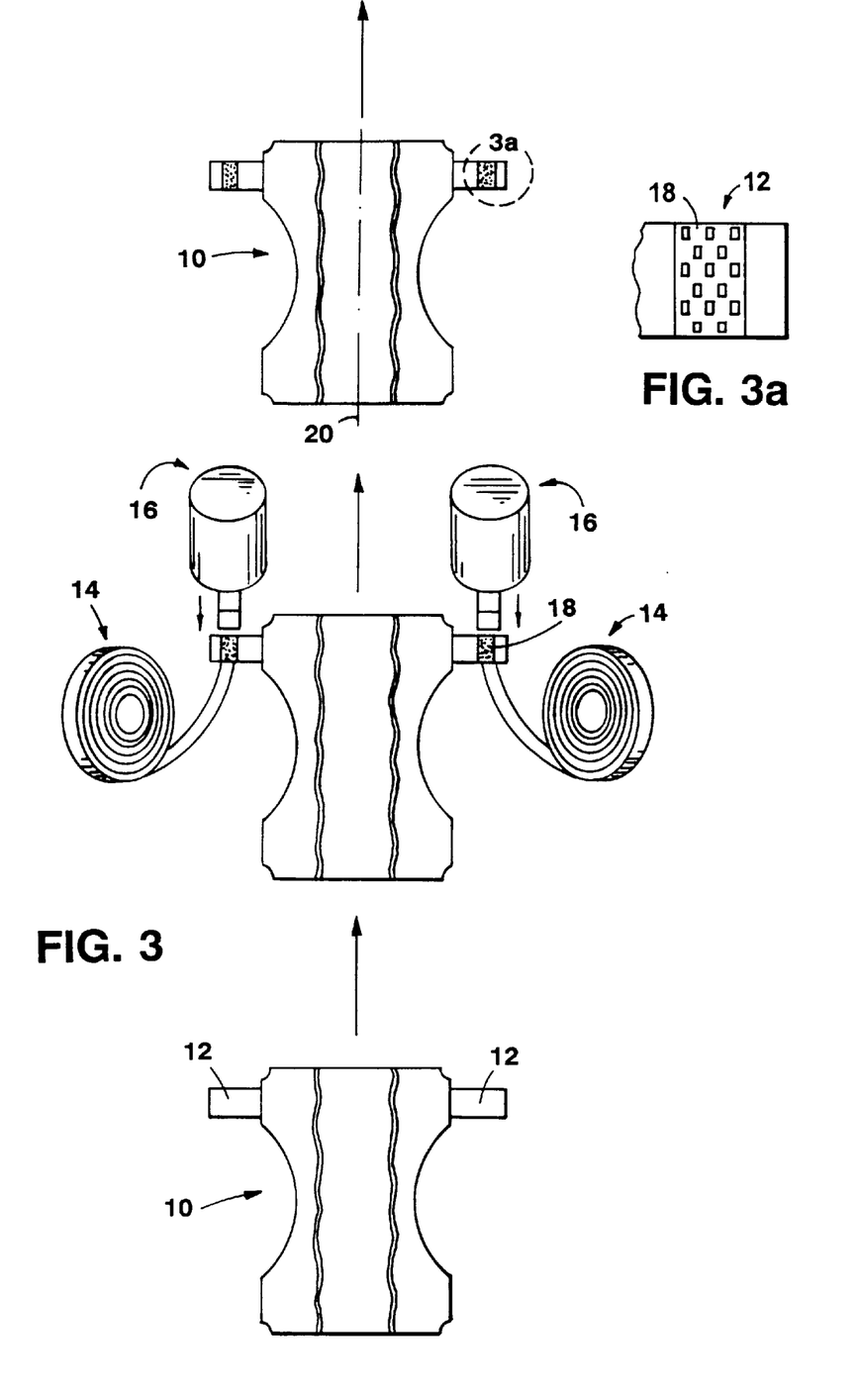
FIG. 3 is a schematic representation of an assembly line in which fastener members as shown in FIGS. 1 and 2 are applied to diapers.
FIG 3a is a blow-up of a portion of FIG. 3 showing the orientation of the fastener elements on the diaper.

As shown in FIGS. 3 and 3a, disposable diapers 10 commonly are made on an assembly line with the fastener tabs 12 extending to the sides, perpendicular to the direction in which the diapers travel. The hook fastener member is provided in large rolls 14 of hook fastener tapes. As explained below, the hook fastener tapes are made using a rotating molding roll in which the hook elements are aligned with the circumference of the roll. As a result of that process, the hook-form fastener elements are aligned along the lengthwise direction of the fastener tapes. For manufacturing efficiency, the hook fastener tapes may be unwound and fed out running parallel to the line of diapers. As each diaper passes the appropriate station, a bonding apparatus 16 such as an ultrasonic welder attaches a patch 18 of hook fastener material to each of the fastener tabs 12. As a result, the hook fastener elements are oriented parallel to the longitudinal axis 20 of the diapers, as shown in greater detail in FIG. 3a. Alternatively, the fastener tabs 12 having hook fastener material 18 attached thereto may be formed in a separate process and the fastener tab attached to the diaper during the diaper manufacturing process. Such a separate process is described, for example, in PCT Application Publication No. WO95/05140 which is hereby incorporated by reference.

Figure 4:
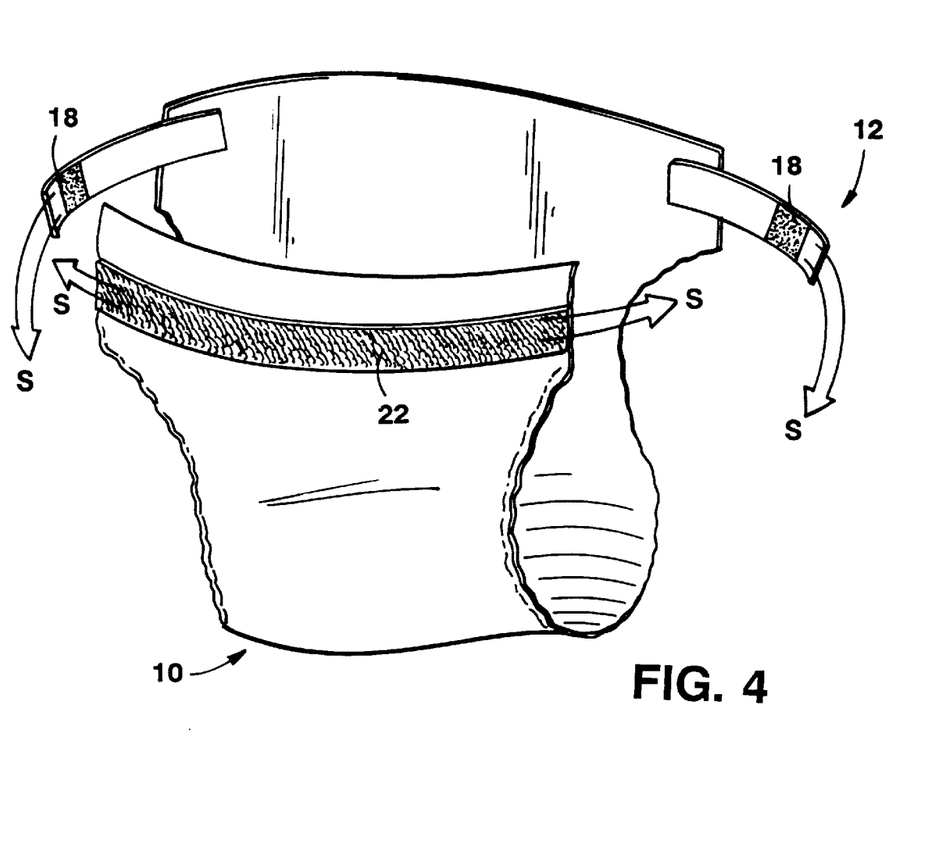
FIG. 4 illustrates the direction of stress applied to the fastener elements during normal use.

When the diaper is put on a baby, it will have the configuration and orientation shown in FIG. 4. Hence, when the fastener tabs 12 are engaged with the mating non-woven loop member strip 22, the tensile forces S applied to the base of the fastener member and the loop member will act perpendicular to the orientation of the hook-form fastener elements, thereby subjecting the closure to lateral shear forces, as suggested in FIG. 5.

Figure 5:
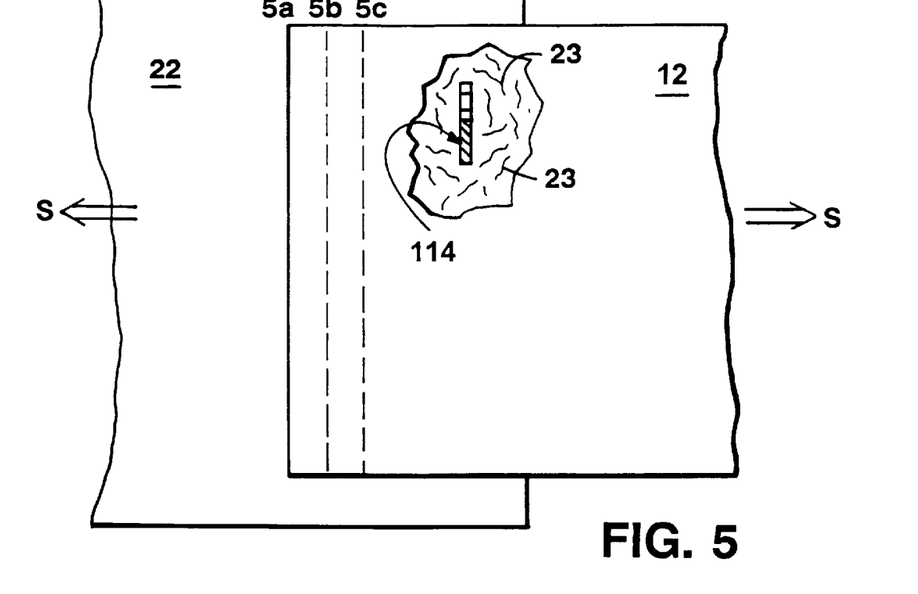
Figure 5A:
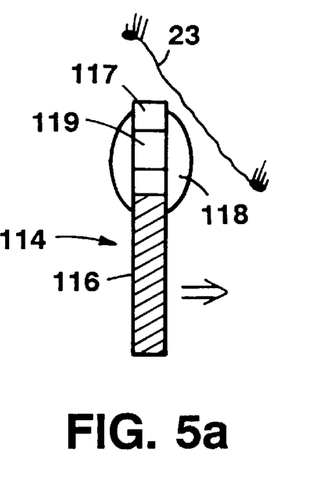
FIGS. 5a, 5b, and FIG. 5c are sequential diagrams illustrating the engagement of a hook fastener element with a loop of a non-woven fabric.
Figure 5B:
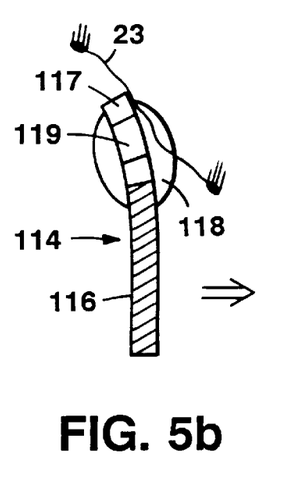
Figure 5C:
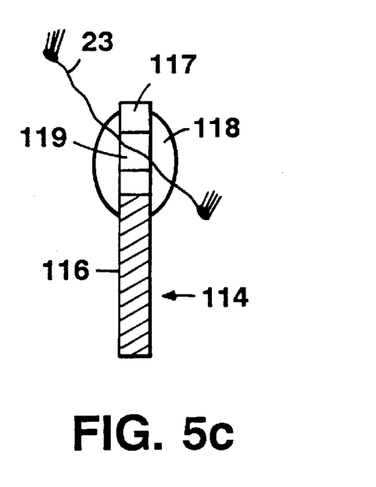

During fastening the fastener tabs 12 will slide slightly relative to the loop member strip 22. This is indicated schematically in FIG. 5, which, with exaggeration for purposes of illustration, shows the edge of the fastener tab 12 at three successive locations 5a, 5b, and 5c. In FIG. 5 there is a "peer-through window" depiction of a single fastener element 114 surrounded by the surface fibers 23 of the non-woven loop member 22, as seen from below the fastener element. As depicted in FIGS. 5a, 5b, and 5c, which correspond in FIG. 5 to the locations 5a, 5b, and 5c, respectively, as the fastener element slides slightly, it is shown to intercept a surface fiber 23 which is depicted as anchored to member 12. During the initial sliding action, an overhanging portion of the thin outer plate 118 of the fastener element slides under the low-lying surface fiber 23 (FIG. 5b), as an initial part of the engaging action. As relative motion continues, the fiber is guided by the fillets 120 between the plate portion 118 and the hook-form portion 117 and the stem portion (see FIG. 1b). The fiber 23 is thus guided under the hook-form portion 117 and is secured in the re-entrant fiber-retaining recess 119 to more securely engage the fastener member with the fiber.

In FIG. 5b, the end of the hook element is shown to have been deflected sideways by the force of engagement with the loop member (shown exaggerated for purposes of illustration). This bending, facilitated by the relative thinness (dimension 136) of the element and the off-center loading on the head of the fastener element is seen to contribute to the effectiveness of the engaging action.

Figure 6:
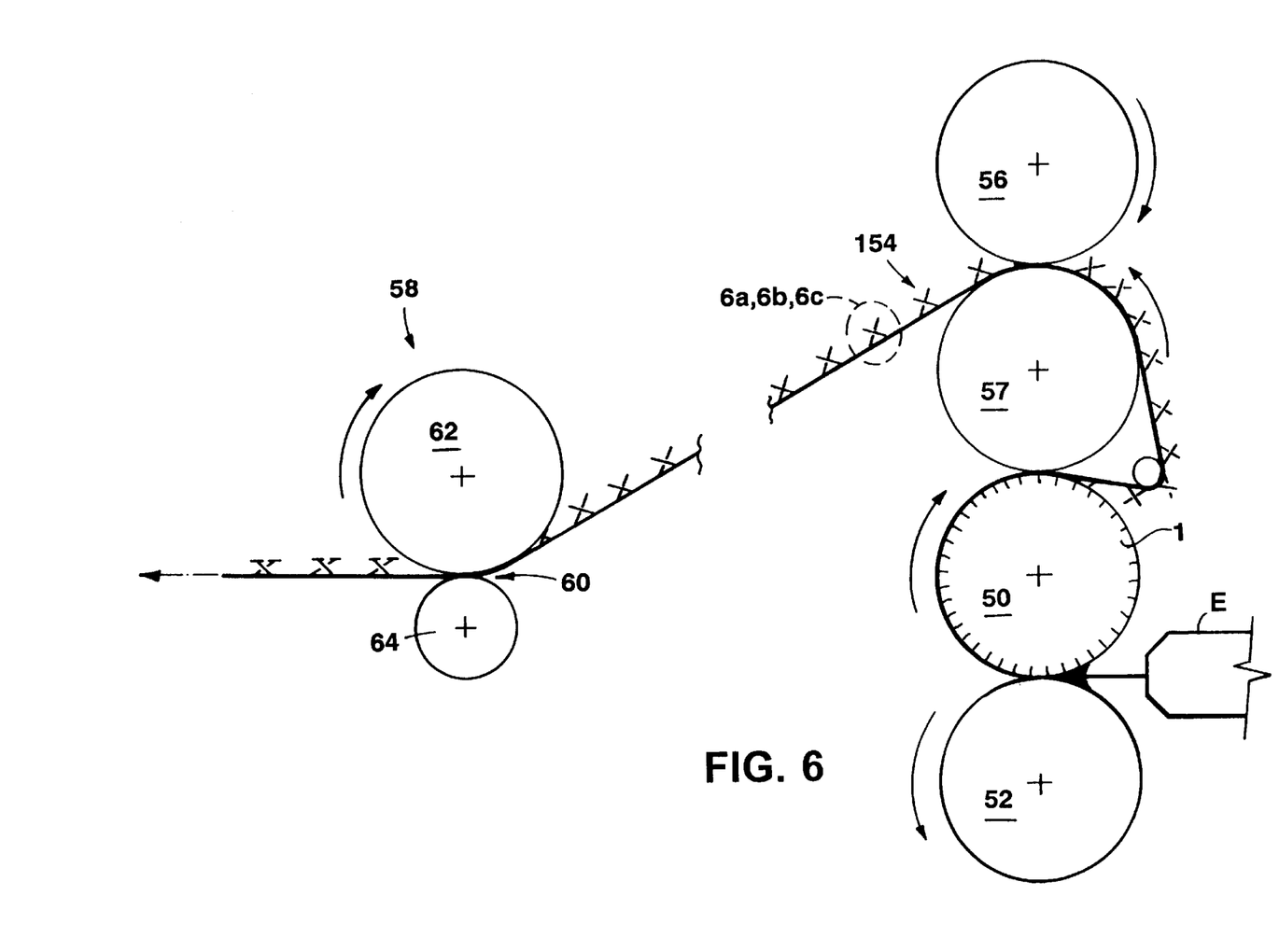
FIG. 6 is a schematic representation of the manufacturing process used to make hook fastener members.

As shown in FIG. 6, a preferred method for making such flat-top hook fastener members entails extruding molten resin into the nip formed between a cooled molding roller 50 and a pressure-applying roller 52, as taught by Fischer, U.S. Pat. No. 4,794,028, fully incorporated herein by reference. The cooled molding roller has cavities about its periphery that are configured to produce fastener element preforms 154, which are shown in greater detail in FIG. 6a.

Because the fastener element preforms face in opposite directions, the fastener element preforms in half the columns are oriented along the direction of travel of the tape, and the fastener element preforms in the other half of the columns are oriented opposite to the direction of travel of the tape. The fastener element preforms that are oriented against the direction of travel can leave the mold cavities of the moving roll without significant bending, but the fastener element preforms that are oriented along the direction of travel are bent around the edges of the mold cavities as they are extracted from the cavities. This deforms them slightly, causing them to extend higher from the base sheet and at a slightly steeper angle than the preforms that are oriented along the direction of travel.

For making the two sets of preforms more uniform, the preforms are passed under a knock-down roller 56, the spacing of which, relative to wrap-around roller 57, is adjustable. The knock-down roller pushes the higher and steeper preforms back to the same level, relative to the base sheet, as the level of the preforms that are oriented with the direction of travel of the tape. This leveling will permit more uniform formation of the plate portions 118, discussed below. The knock-down roller 56 is located close to the position where the preforms are withdrawn from the cavities so that the preforms are still slightly soft and permanently deformable when they pass under the knock-down roller and thus retain their new shape.

Alternatively, to form the plate portion on only some of the fastening elements preforms, the knock down roller 56 can be removed. In this manner, the elements oriented against the direction of travel are left in an elongated, higher state and may be deformed to form plate portions 118 without forming plate portions on the elements oriented along the direction of travel.

After the preforms have cooled sufficiently to be strong enough to withstand pressure applied to them without being deformed, the thin, outer plate portions 118 are formed, as at station 58. The plate portions can be formed either in line with the molding process, i.e., as part of a continuous operation, or they can be formed in a separate, post-forming operation at some later time. Hence, the fastener tape is shown as broken in FIG. 6 to indicate this variability.

To form the outer plate portions, the tape of fastener element preforms is passed through gap 60 between a thermo-forming heated roller 62 and a support roller 64, the gap width of which is adjustable. Roller 62 is heated to a selected temperature sufficient to thermally reform the elements. Thus, as the preforms come into contact with the heated thermo-forming roller 62, their outer ends 155 (FIG. 6a) are thermo-formed by the action of the rollers to provide the disk-shaped plate portions 118 of the fastener elements 114.

The selected temperature of roller 62 depends upon the thermal properties of the particular resin being used to make the fastener member and the selected speed of operation. Presently, the shell material of disposable diapers is often polypropylene. In certain applications, nylon or other materials would also be appropriate. To ensure good bonding when the hook fastener members are attached to the fastener tabs of the diapers 12, the hook fastener member is also preferably made from polypropylene. In this case, the roller 62 is heated to a surface temperature of approximately 350° Fahrenheit, and has operated in a demonstration line at lineal speed of approximately 11 feet per minute (Much higher speeds will be used in production.). The preforms approach the roller 62 nearly tangentially. This results in a temperature at the hook surface which is approximately the same as the melt temperature of the polypropylene resin, and causes the end of the preform to be softened to the point of being permanently deformable under pressure, without being caused to melt to a highly fluid state.

It is, of course, foreseeable that other plastics will be used to form such flat-top hook fastener members. The material selected preferably has a relatively low melt flow index, which is a measure of the viscosity of the resin when it is molten. Resins with fractional melt flow indices, i.e., indices that are less than 1.0, are most preferred, although under certain circumstances and hook designs, resins with melt flow indices as high as 5.0 or 10.0, or even higher, can be used by careful balancing of the steps of the process. The temperature of the roller 62 and the lineal speed through the station 58 are selected to impart a temperature to the hook surface which renders the selected resin moldable. For polypropylene, as noted above, it was found that 350° Fahrenheit was appropriate. Further, additional support rollers and the like may be employed to increase the arc of the roller 62 which the preforms contact, thereby increasing the heating time for a given lineal speed.

The width of the gap 60 between thermo-forming roller and support roller 64 is adjusted to obtain the appropriate height 130 (FIG. 1a) of the final fastener elements, the height 130 in turn being a function of the height of the fastener element preforms. With regard to the amount by which the tops of the hook elements are thermoformed, and therefore with regard to the height 30, it is important that the outer ends not be deformed so much as to impair the geometry of hook-form portion 117 or the ability of the fastener element to engage and retain the fibers of the loop member.

In general, the tops of the elements are thermoformed by an amount to produce an effective overhang of the plate portion, i.e., the amount by which the plate portion extends beyond (overhangs) either side 116a, 116b of the stem portion of the fastener element. Depending upon the conditions of use, it is advantageous for the amount of overhang to fall within the range of 5 to 50% of the thickness of the hook element; in other conditions with the range of 10 to 30%; and in other conditions, within the range of 15 to 25%. In certain preferred instances, the overhang is about 25% of the thickness of the stem portion. Thus, in preferred cases the widthwise dimension 138 of the plate portions (FIG. 2) is approximately 1.5 to 2.0 times the thickness 136 of the stem portion and the vertical thickness 139 of the plate portion 118 is between about 0.2 and 0.4 times the thickness 136 of the stem portion. The lengthwise dimension of the plate portion, in general, will be somewhat longer than the widthwise dimension, and it is generally allowed to be whatever dimension results from thermoforming the plate portion sufficiently to obtain the desired effective sideways overhang and hook height. The thickness of one plate was 0.002 inch and the overhang was 0.003–0.004 inch. A preferred thickness range is 0.0001 to 0.005 inch, and in certain instances a more preferred range is 0.001 to 0.004 inch.

Finally with regard to the manufacturing process, in order for the plate portions 118 to be substantially parallel to the base of the hook fastener member, it is preferred that the heated roller 62 and support roller 64 rotate at speeds such that their tangential surface velocities substantially match the feed rate of the fastener tape. Otherwise, the plate portions will be dragged by, or will drag along, the heated roller and be deformed.

Figure 7:
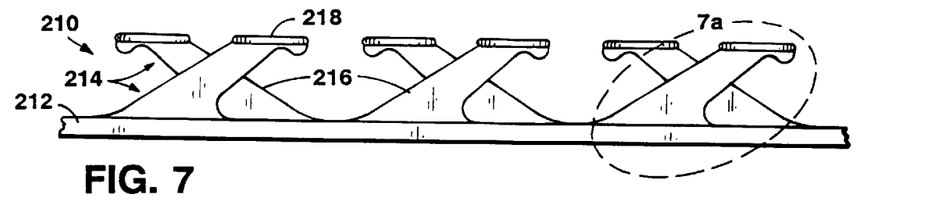
FIGS. 7 and 8 are side elevational and plan views, respectively, showing a second embodiment of a hook fastener member.
Figure 7A:
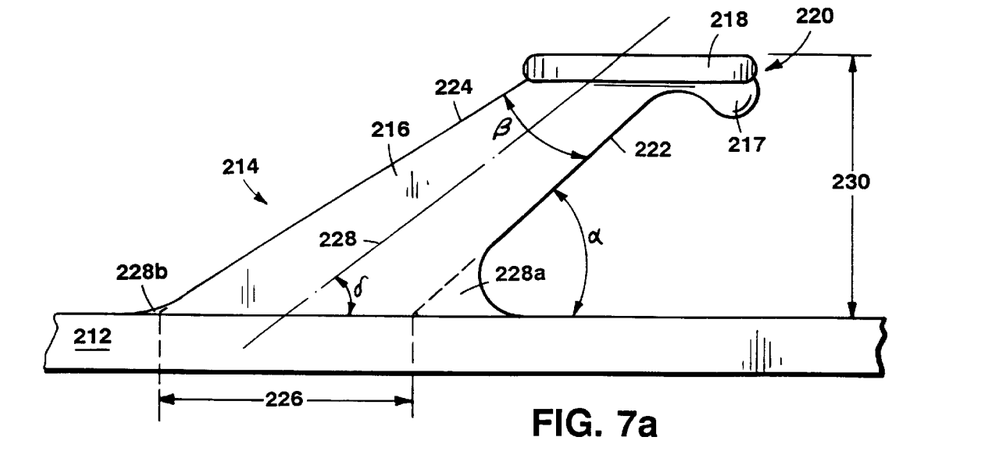
FIG. 7a is a detailed side elevational view showing a fastener element of the fastener member of FIG. 7.
Figure 8:
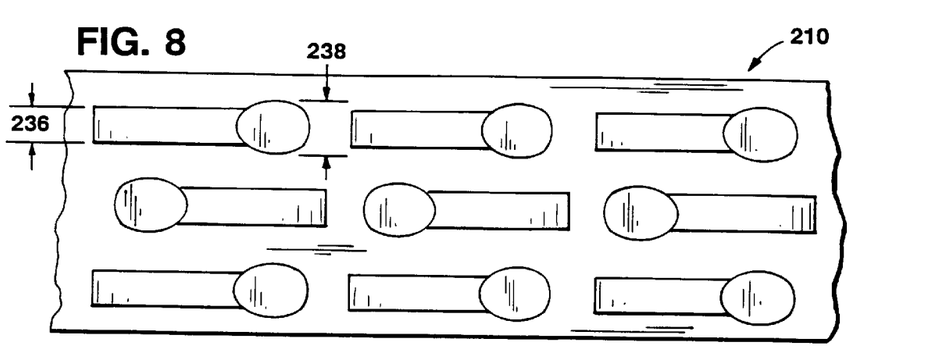

Another preferred embodiment 210 of a flat-top hook fastening member is shown in FIGS. 7, 7a, and 8. This embodiment has a base sheet 212 from which extend a multiplicity of discrete, flat-top fastener elements 214. Each fastener element 214 has a canted stem portion 216, having flat sides similar to sides 116a, 116b of FIG. 1b. These portions are integrally molded with and extend from the base sheet. Each fastener element also has a generally planar, disk-shaped outer plate portion 218 located at the outer end 220 of the stem portion that overhangs the flat sides of the canted stem and a re-entrant hook-form portion 217 depending from the outer plate portion. The plate portion 218 extends generally parallel to the base sheet 212.

As shown in greater detail in FIG. 7a, the general configuration of the stem portion 216 of the fastener elements can be characterized by two parameters. First, it is canted relative to the base 212 in that the surface 222 of the stem portion on the side on which the hook recess is formed forms an acute cant angle $\alpha$ relative to the base. Preferably, cant angle $\alpha$ is between about 30 degrees and about 80 degrees; more preferably, $\alpha$ is between about 40 and 60 degrees, and most preferably, $\alpha$ is about 45 degrees.

The second parameter to characterize the configuration of the stem portion is the base width 226 which, as before, is the width of the stem portion, taken parallel to the base sheet 212 where the stem portion joins the base, disregarding the fillets 228a and 228b. Preferably, the base width is between about 0.010 inch and about 0.018 inch; more preferably, the base width is about 0.014 inch.

Finally, other parameters that characterize the entire fastener element 214 are the height 230 of the fastener element, as measured from the top surface of the base sheet 212 to the top surface of the plate portion 218, and the widthwise dimension 238 of the plate portion. The thickness of the stem portion 236 is preferably the same as for the first embodiment, e.g., about 0.006 inch. Preferably, the height is between about 0.005 inch and about 0.030 inch; more preferably, the height is about 0.015 inch.

As shown in FIGS. 7 and 8, the fastener elements 214 are arranged on the base sheet 212 with the fastener elements in one column all canted in one direction and the fastener elements in the adjacent column all canted in the opposite direction. The spacing and density of the fastener elements is approximately the same as the spacing and density described above with respect to the first embodiment.

Figure 6A:
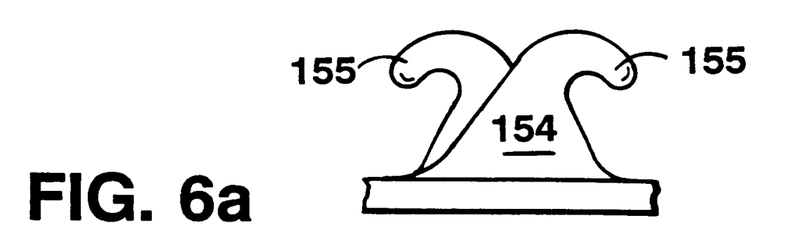
FIGS. 6a, 6b, and 6c are side elevational views showing fastener element preforms used to make hook fastener members.
Figure 6B:
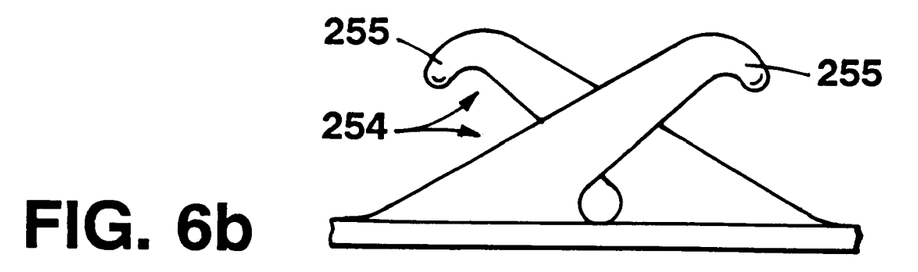

The embodiment of the flat-top hook fastener member of FIGS. 7 and 8 is also made by the process shown in FIG. 6. The hook preforms 254 are configured as shown in FIG. 6b which, like the preforms 154 shown in FIG. 6a, are generally of hook shape, although canted relative to the base. Other profiles for a canted hook preform 254 can also be used. See, for example, FIG. 22 of Provost et al., U.S. Pat. No. 4,984,339, which is incorporated by reference.

Figure 9:
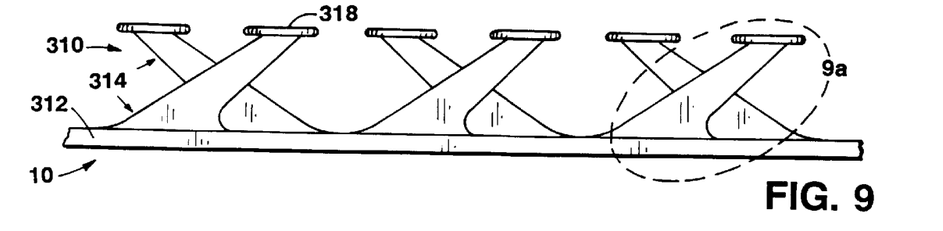
FIGS. 9 and 10 are side elevational and plan views, respectively, showing a third embodiment of a hook fastener member.

The canted relationship of fasteners elements of FIGS. 7 and 9 provide a longer fastener element and a greater degree of off-center loading when subjected to conditions as depicted in FIG. 4 of the preceding embodiment. As a result, under loading conditions depicted in FIG. 4, a greater degree of elastic deflection of the hook end can occur that can increase the fiber-engaging effectiveness of the hook elements.

Figure 6C:
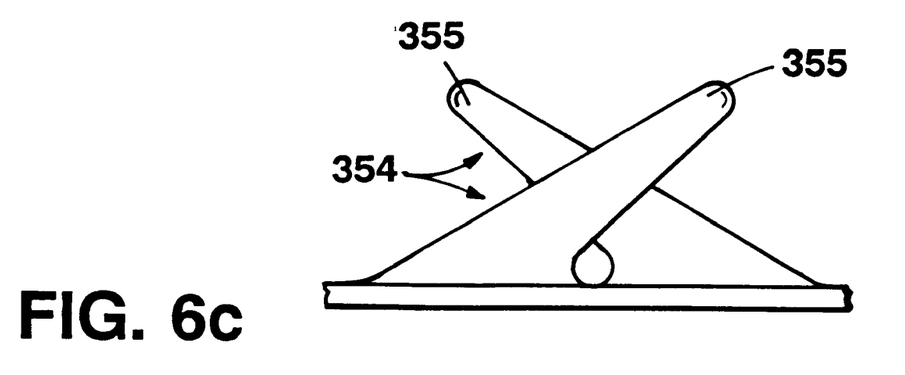
Figure 9A:
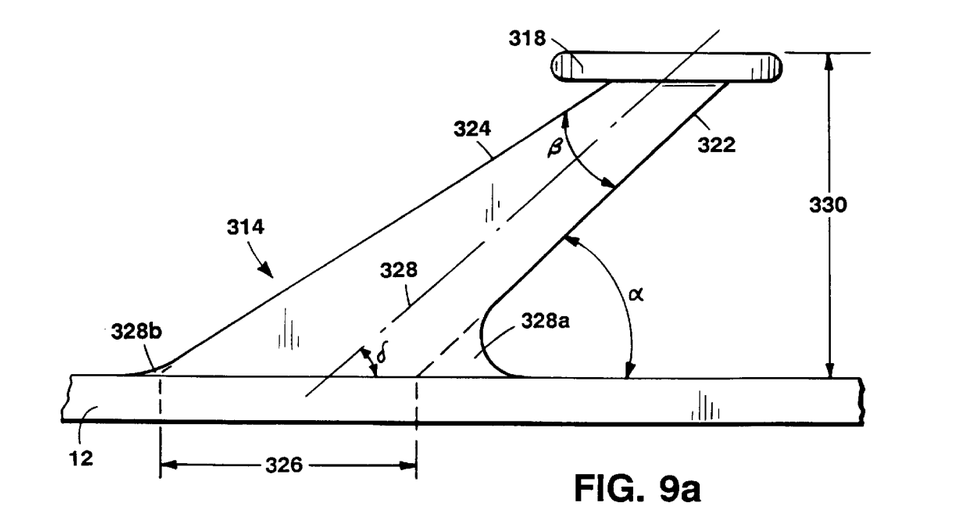
FIG. 9a is a detailed side elevational view showing a fastener element of the fastener member of FIG. 10.
Figure 10:
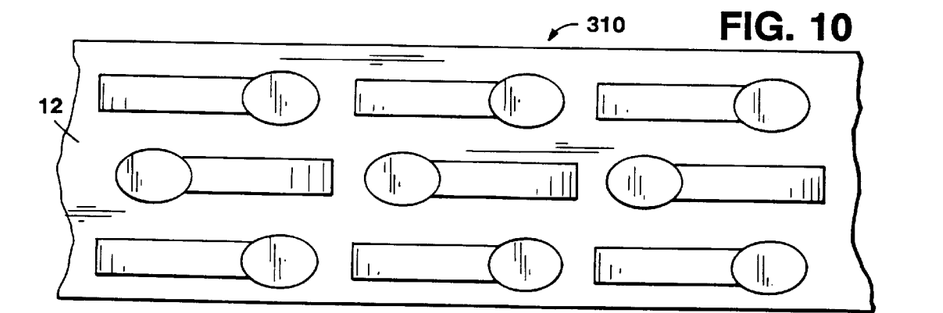

A third preferred embodiment 310 of a flat-top hook fastener member is shown in FIGS. 9, 9a, and 10. This embodiment is similar to the second embodiment 210 discussed above, the outer plate overhanging the flat sides of the canted stem. The primary difference in this embodiment is that the intersection of the canted stem and the outer plate 318 defines a fiber-engaging hook that is not re-entrant. This enables the overhanging plate portion 318 to slide under loop members with extremely low-lying loft. The third embodiment is also manufactured by the method shown in FIG. 6, this time using simple tapered fastener element preforms 354 without re-entrant hooks, as shown in FIG. 6c.

As described above, when the fastener element performs face in opposite directions, the fastener element preforms that are oriented along the direction of travel are bent around the edges of the mold cavities as they are extracted. This causes these preforms to extend higher from the base sheet and at a slightly steeper angle than the preforms that are oriented along the direction of travel.

Figure 11:
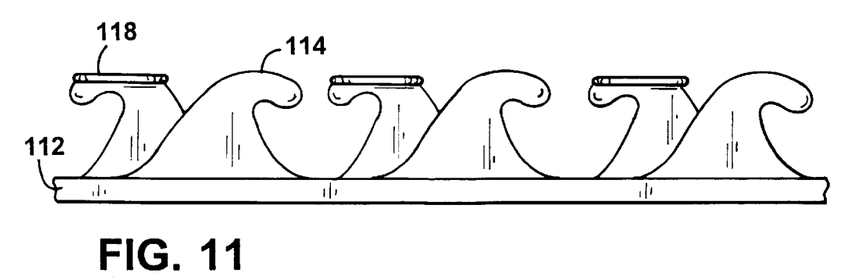
FIGS. 11 and 12 are side elevational and plan views, respectively, of a fourth embodiment of a hook fastener member.
Figure 12:
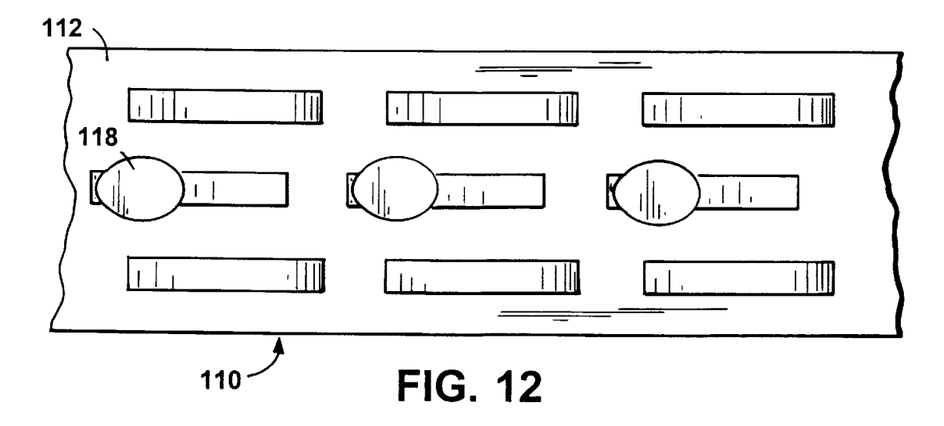

In certain instances is desirable to form the outer plate portions 118 on only some of the fastener element preforms. This can be achieved, for example, by not passing the fastener element preforms under the knock-down roller 56. Thus, since the fastener element preforms have different heights from the base sheet, passing the fastener element preforms through gap 60 between the heated roller 62 and support roller 64 will form the disk-shaped plate portions 118 on only those fastener element preforms which extend furthest from the base sheet (those preforms that are oriented along the direction of travel) as shown in FIGS. 11 and 12. For some applications, having some of the fastener element preforms possess the disk-shaped plate portions 118 and others not possess the plate portions provides for a more satisfactory balance of fastening properties (such as a desired balance of peel and shear properties). In other embodiments the fastener element preforms are formed to have different heights from the base sheet independent of their orientation during manufacture. This is accomplished through the use of mold cavities having different depths during formation of the preforms. With such preforms, in one embodiment flat tops are provided only on those preforms having the greatest height. Forming the fastener element preforms to have different heights from the base sheet in some instance allows greater control over the percentage of elements that are "flat topped." It is possible to form fastener element preforms with two, three or more different heights from the base sheet.

Other embodiments are within the scope of the following claims.

What is claimed is:

1. A fastener member comprising a base, and multiple rows of fastener elements extending from said base and exposed for engagement with a fabric, each fastener element integrally molded with and extending from the base to a distal end, each fastener element molded to overhang the base in the direction of the rows to enable engagement of fabric fibers between the fastener element, as molded, and the base;

at least some of the fastener elements each having a fiber-engaging plate portion at its distal end, the plate portion lying generally parallel to the base and overhanging the base in a direction perpendicular to its respective row of elements to enable additional engagement of fabric fibers between the plate portion and the base.

2. The fastener member of claim 1 wherein said fastener elements with plate portions each have a re-entrant hook-form portion having a free end, said plate portion having a thickness, in a direction normal to said base, that is less than the thickness, in a direction normal to said base, of the free end of said hook-form portion.

3. The fastener member of claim 1 wherein said fastener elements are formed of thermoplastic resin, stem portions of said elements being molded integrally with said said plate portions each comprising a post-formed structure formed of resin of a molded fastener element.

4. The fastener member of claim 1 wherein overhanging portions of substantially all of the fastener elements in a first row extend in a first direction and substantially all of the fastener elements in a neighboring second row extend in a second direction opposite to the first direction.

5. The fastener member of claim 4 in which substantially all of the fastener elements in said first row each include a said plate portion, and substantially all of the fastener elements in said neighboring second row do not include said plate portions.

6. The fastener member of claim 1 wherein said fastener elements with plate portions each have substantially flat broad sides, a cross-section of each fastener element, taken parallel to said base at mid-height of the fastener element, having a width in the direction of the rows and a thickness in the direction perpendicular to the rows, said width being at least about twice said thickness.

7. The fastener member of claim 6 wherein said width tapers inwardly from said base.

8. The fastener member of claim 1 wherein the fastener elements each define a central axis which is inclined, in the direction of the rows, at an acute angle relative to said base.

9. The fastener member of claim 1 in which substantially all of said fastener elements each include a said plate portion.

10. The fastener member of claim 1 formed by the process of forming a preform product having multiple rows of preform elements extending from a base, the preform elements extending in the direction of their rows and each comprising a stem portion integrally molded with the base, and at least one fiber-engaging portion extending from the stem portion and overhanging the base in the direction of extent of its respective row; and passing the preform elements against a heated surface to melt outermost portions of at least some of said fiber-engaging portions to form said plate portions.

11. The fastener member of claim 10 wherein the preform elements are hook-shaped.

12. The fastener member of claim 10 wherein the heated surface comprises the surface of a roller.

13. The fastener member of claim 1 wherein the fastener elements each have at least one flat side, the plate portions extending from the flat side of their respective fastener elements to overhang the base.

14. The fastener member of claim 1 wherein each fastener element overhangs the base in the direction of the rows to define a first recess for engaging fibers;

the plate portions defining additional recesses, farther from the base than the first recess, for engaging additional fibers.

15. A fastener member comprising a base, and multiple rows of molded fastener elements extending from said base, each said fastener element comprising a stem portion integrally molded with said base, said stem portion being inclined at an acute angle relative to the base to overhang the base in the direction of the respective row of said fastener element;

at least some of the fastener elements each having a fiber-engaging plate portion disposed at an outermost end thereof, said plate portions extending transversely to the direction of extent of the rows to form overhang portions on two opposite sides of their respective fastener elements.

16. The fastener member of claim 15 in which substantially all of said fastener elements each include a said plate portion.

17. The fastener member of claim 15 wherein a cross-section of each said stem portion, taken parallel to said base, has a width in the direction of extent of the rows and a thickness in the direction perpendicular to the extent of the rows, said width being substantially greater than said thickness.

18. A closure comprising the fastener member of claim 6 or claim 17 and a non-woven fabric engaged therewith, the base of said fastener and said non-woven fabric being under tension in opposite directions such that said fastener elements are subjected to and resist shear forces caused by said tension loading, the tension acting in the direction of said thickness.

19. The fastener member of claim 15 wherein the fastener elements with plate portions are taller than some fastener elements without plate portions.

* * * * *